United States Patent
Furfine et al.

(10) Patent No.: US 11,732,024 B2
(45) Date of Patent: *Aug. 22, 2023

(54) VEGF ANTAGONIST FORMULATIONS SUITABLE FOR INTRAVITREAL ADMINISTRATION

(71) Applicant: REGENERON PHARMACEUTICALS, INC., Tarrytown, NY (US)

(72) Inventors: Eric Furfine, Concord, MA (US); Daniel Dix, LaGrangeville, NY (US); Kenneth Graham, Pleasant Valley, NY (US); Kelly Frye, Mendham, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 138 days.

This patent is subject to a terminal disclaimer.

(21) Appl. No.: 17/348,438

(22) Filed: Jun. 15, 2021

(65) Prior Publication Data
US 2021/0340220 A1 Nov. 4, 2021

Related U.S. Application Data

(60) Continuation of application No. 16/582,486, filed on Sep. 25, 2019, now Pat. No. 11,066,458, which is a continuation of application No. 16/159,269, filed on Oct. 12, 2018, now Pat. No. 10,464,992, which is a continuation of application No. 15/879,294, filed on Jan. 24, 2018, now Pat. No. 10,400,025, which is a continuation of application No. 15/095,606, filed on Apr. 11, 2016, now Pat. No. 9,914,763, which is a continuation of application No. 14/330,096, filed on Jul. 14, 2014, now Pat. No. 9,340,594, which is a continuation of application No. 13/914,996, filed on Jun. 11, 2013, now Pat. No. 8,802,107, which is a continuation of application No. 13/329,770, filed on Dec. 19, 2011, now Pat. No. 8,481,046, which is a continuation of application No. 12/833,417, filed on Jul. 9, 2010, now Pat. No. 8,092,803, which is a continuation of application No. 12/560,885, filed on Sep. 16, 2009, now Pat. No. 7,807,164, which is a division of application No. 11/818,463, filed on Jun. 14, 2007, now Pat. No. 7,608,261.

(60) Provisional application No. 60/814,484, filed on Jun. 16, 2006.

(51) Int. Cl.
| A61K 38/17 | (2006.01) |
| C07K 14/71 | (2006.01) |
| A61K 9/00 | (2006.01) |
| A61K 9/19 | (2006.01) |
| C07K 14/47 | (2006.01) |
| A61M 5/178 | (2006.01) |
| A61K 47/26 | (2006.01) |
| A61K 47/02 | (2006.01) |
| A61K 47/10 | (2017.01) |

(52) U.S. Cl.
CPC ............ *C07K 14/71* (2013.01); *A61K 9/0019* (2013.01); *A61K 9/0048* (2013.01); *A61K 9/19* (2013.01); *A61K 38/179* (2013.01); *A61K 38/1793* (2013.01); *A61K 47/02* (2013.01); *A61K 47/10* (2013.01); *A61K 47/26* (2013.01); *A61M 5/178* (2013.01); *C07K 14/47* (2013.01); *C07K 14/4705* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,399,670 A | 3/1995 | Bhattacharya et al. |
| 5,763,401 A | 6/1998 | Nayar et al. |
| 5,851,999 A | 12/1998 | Ulrich et al. |
| 6,011,003 A | 1/2000 | Charnock-Jones et al. |
| 6,100,071 A | 8/2000 | Davis-Smyth et al. |
| 6,171,586 B1 | 1/2001 | Lam et al. |
| 6,267,958 B1 | 7/2001 | Andya et al. |
| 6,270,993 B1 | 8/2001 | Shibuya et al. |
| 6,472,179 B2 | 10/2002 | Stahl et al. |
| 6,676,941 B2 | 1/2004 | Thorpe et al. |
| 6,833,349 B2 | 12/2004 | Xia et al. |
| 6,875,432 B2 | 4/2005 | Liu et al. |
| 6,897,294 B2 | 5/2005 | Davis-Smyth et al. |
| 7,001,892 B1 | 2/2006 | Chmielweski et al. |
| 7,052,691 B2 | 5/2006 | Sleeman et al. |

(Continued)

FOREIGN PATENT DOCUMENTS

| | | |
|---|---|---|
| CA | 2569108 A1 | 12/2005 |
| CA | 2598711 | 10/2006 |

(Continued)

OTHER PUBLICATIONS 4.1.3. Buffer solutions, European Pharmacopoeia 5.0, 431-434 (2004).
Amand et al., Controllability analysis of protein glycosylation in CHO cells, PLOS One, 9(2): e87943 (2014) (16 pgs).
Amersham Biosciences, Antibody Purification Handbook, 18-1037-46, pp. 5-107 (2002).
AMEVIVE® Label (Issued Sep. 2005) (2 pgs.).
Annex 1 (D21), filed in Opposition to European Patent No. 2 944 306 B1, 1 pg. (2021).

(Continued)

*Primary Examiner* — Christine J Saoud
*Assistant Examiner* — Jon M Lockard
(74) *Attorney, Agent, or Firm* — Arnold & Porter Kaye Scholer LLP

(57) ABSTRACT

Ophthalmic formulations of a vascular endothelial growth factor (VEGF)-specific fusion protein antagonist are provided suitable for intravitreal administration to the eye. The ophthalmic formulations include a stable liquid formulation and a lyophilizable formulation. Preferably, the protein antagonist has an amino acid sequence of SEQ ID NO:4.

60 Claims, No Drawings

Specification includes a Sequence Listing.

(56) References Cited

U.S. PATENT DOCUMENTS

| | | |
|---|---|---|
| 7,060,268 B2 | 6/2006 | Andya et al. |
| 7,070,959 B1 | 7/2006 | Papadopoulos et al. |
| 7,087,411 B2 | 8/2006 | Daly et al. |
| 7,374,757 B2 | 5/2008 | Papadopoulos et al. |
| 7,374,758 B2 | 5/2008 | Papadopoulos et al. |
| 7,482,002 B2 | 1/2009 | Cedarbaum |
| 7,608,261 B2 | 10/2009 | Furfine |
| 7,750,138 B2 | 7/2010 | Fang et al. |
| 7,807,164 B2 | 10/2010 | Furfine et al. |
| 7,951,585 B2 | 5/2011 | Ke |
| 8,084,234 B2 | 12/2011 | Papadopoulos et al. |
| 8,092,803 B2 | 1/2012 | Furfine et al. |
| 8,110,546 B2 | 2/2012 | Dix et al. |
| 8,216,575 B2 | 7/2012 | Yu |
| 8,343,737 B2 | 1/2013 | Papadopoulos et al. |
| 8,404,638 B2 | 3/2013 | Dix et al. |
| 8,481,046 B2 | 7/2013 | Furfine et al. |
| 8,647,842 B2 | 2/2014 | Papadopoulos et al. |
| 8,710,004 B2 | 4/2014 | Dix et al. |
| 8,802,107 B2 | 8/2014 | Furfine et al. |
| 8,921,316 B2 | 12/2014 | Dix et al. |
| 9,340,594 B2 | 5/2016 | Furfine |
| 9,416,167 B2 | 8/2016 | Dix et al. |
| 9,511,140 B2 | 12/2016 | Dix et al. |
| 9,580,489 B2 | 2/2017 | Furfine |
| 9,636,400 B2 | 5/2017 | Dix et al. |
| 9,657,084 B2 | 5/2017 | Ke et al. |
| 9,914,763 B2 | 3/2018 | Furfine et al. |
| 10,400,025 B2 | 9/2019 | Furfine et al. |
| 10,406,226 B2 | 9/2019 | Dix et al. |
| 1,046,492 A1 | 11/2019 | Furfine et al. |
| 10,464,992 B2 | 11/2019 | Furfine et al. |
| 10,857,231 B2 | 12/2020 | Dix et al. |
| 11,066,458 B2 | 7/2021 | Furfine et al. |
| 11,084,865 B2 | 8/2021 | Furfine et al. |
| 2001/0014326 A1 | 8/2001 | Andya et al. |
| 2002/0004478 A1 | 1/2002 | Danko et al. |
| 2003/0092606 A1 | 5/2003 | L'Italien et al. |
| 2003/0113316 A1 | 6/2003 | Kaisheva et al. |
| 2003/0138417 A1 | 7/2003 | Kaisheva et al. |
| 2003/0202972 A1 | 10/2003 | Andya et al. |
| 2004/0014667 A1 | 1/2004 | Daly et al. |
| 2004/0197324 A1 | 10/2004 | Liu et al. |
| 2004/0213787 A1 | 10/2004 | Sleeman et al. |
| 2004/0265309 A1 | 12/2004 | Kandel et al. |
| 2004/0266688 A1 | 12/2004 | Nayak |
| 2005/0004027 A1 | 1/2005 | Wiegand et al. |
| 2005/0032699 A1 | 2/2005 | Holash et al. |
| 2005/0043236 A1 | 2/2005 | Daly et al. |
| 2005/0112061 A1 | 5/2005 | Holash et al. |
| 2005/0276808 A1 | 12/2005 | Cedarbaum |
| 2005/0281822 A1 | 12/2005 | Cedarbaum et al. |
| 2005/0281831 A1 | 12/2005 | Davis-Smyth et al. |
| 2006/0030000 A1 | 2/2006 | Alitalo et al. |
| 2006/0058234 A1 | 3/2006 | Daly et al. |
| 2006/0217311 A1 | 9/2006 | Dix et al. |
| 2008/0085276 A1 | 4/2008 | Wiegand et al. |
| 2009/0264358 A1 | 10/2009 | Yu et al. |
| 2012/0101035 A1 | 4/2012 | Dix et al. |
| 2012/0178683 A1 | 7/2012 | Dix et al. |
| 2013/0261056 A1 | 10/2013 | Dix et al. |
| 2014/0012227 A1 | 1/2014 | Sigg et al. |
| 2015/0079087 A1 | 3/2015 | Dix et al. |
| 2016/0144025 A1 | 5/2016 | Vitti et al. |
| 2016/0175439 A1 | 6/2016 | Dix et al. |
| 2017/0073407 A1 | 3/2017 | Dix et al. |
| 2017/0360930 A1 | 12/2017 | Dix et al. |

FOREIGN PATENT DOCUMENTS

| | | |
|---|---|---|
| CN | 1304427 C | 3/2007 |
| CN | 100502945 C | 6/2009 |
| CN | 100567325 C | 12/2009 |
| CN | 102233132 B | 10/2013 |
| CN | 102380096 B | 4/2014 |
| CN | 103212075 B | 6/2017 |
| CN | 107115294 A | 9/2017 |
| EP | 2944306 | 1/2021 |
| JP | 10273450 | 10/1998 |
| JP | H10273450 | 10/1998 |
| JP | H11510170 | 9/1999 |
| JP | 2002516871 | 6/2002 |
| WO | WO 1993/000807 A1 | 1/1993 |
| WO | WO 97/04801 | 2/1997 |
| WO | WO 1998/045331 | 10/1998 |
| WO | WO 1998/045331 A2 | 10/1998 |
| WO | WO 1999/013909 A1 | 3/1999 |
| WO | WO 99/62536 | 12/1999 |
| WO | WO 00/63380 | 10/2000 |
| WO | WO 2000/075319 | 12/2000 |
| WO | WO 2000/075319 A2 | 12/2000 |
| WO | WO 2002/060489 | 8/2002 |
| WO | WO 2003/072060 A2 | 9/2003 |
| WO | WO 2004/087206 A2 | 10/2004 |
| WO | WO 2004/091658 | 10/2004 |
| WO | WO 2004/103159 A2 | 12/2004 |
| WO | WO 2004/106378 A3 | 12/2004 |
| WO | WO 2005/000895 | 1/2005 |
| WO | WO 2005/011734 | 2/2005 |
| WO | WO 2005/020972 | 3/2005 |
| WO | WO 2005/072772 A1 | 8/2005 |
| WO | WO 2005/102303 A2 | 11/2005 |
| WO | WO2006/015297 | 2/2006 |
| WO | WO 2006/047325 | 5/2006 |
| WO | WO 2006/088650 | 8/2006 |
| WO | WO 2006/104852 | 10/2006 |
| WO | WO 2006/138181 A2 | 12/2006 |
| WO | WO 2007/112675 | 10/2007 |
| WO | WO 2007/149334 A2 | 12/2007 |

OTHER PUBLICATIONS

Arakawa et al., "Protein-Solvent Interactions in Pharmaceutical Formulations," Pharmaceuticals Research, 8(3):285-291 (1991).
Avastin® (Bevacizumab) label, Center for Drug Evaluation and Research Approval Package for: Application No. STN-125085/0, pp. 1-28 (2004).
Avery et al., "Intravitreal Bevacizumab (Avastin) for Neovascular Age-Related Macular Degeneration," *American Academy of Ophthalmology*, 113(3):363-372.e5 (Feb. 2006).
Back et al., "Increased Thermal Stability of Proteins on the Presence of Sugars and Polyols," *Biochemistry*, 18(23):5191-5196 (1979).
Baffert et al., "Age-Related Changes in Vascular Endothelial Growth Factor Dependency and Angiopoietin-l-Induced Plasticity of Adult Blood Vessels," *Circulation Research*, 984-992 (2004).
Bogard, Jr. et al., "Practical Considerations in the Production, Purification, and Formulation of Monoclonal Antibodies for Immunoscintigraphy and Immunotherapy," *Seminars in Nuclear Medicine*, XIX(3):202-220 (1989).
Borys et al., "Culture pH affects expression rates and glycosylation of recombinant mouse placental lactogen proteins by Chinese hamster ovary (CHO) cells," *Biotechnology*, 11:720-724 (1993).
Byrn et al., "Biological properties of a CD4 immunoadhesin," *Nature*, 344:667-670 (1990).
Capon et al., "Designing CD4 immunoadhesins for AIDS therapy," *Nature*, 337:525-531 (1989).
CARBOWAX™ Polyethylene Glycol (PEG) 3350 (1 pg.).
Carpenter et al., "Rational design of stable lyophilized protein formulations: some practical advice," *Pharm. Res.* 14(8): 969-975 (1997).
Chou et al., "Effects of Tween 20® and Tween 80® on the Stability of Albutropin During Agitation," *Journal of Pharmaceutical Sciences*, 94(6):1368-1381 (2005).
Christensen, "Proteins as Buffers," Annals New York Academy of Sciences, 133(1):34-40 (1966).
Cleland et al., "Formulation and Delivery of Proteins and Peptides," American Chemical Society, pp. 1-19 (1994).
Daugherty et al., "Formulation and delivery issues for monoclonal antibody therapeutics," *Adv. Drug Delivery Rev.*, 58:668-706 (2006).
Decision on Petition Under 37 CFR 1.181 dated Sep. 30, 2021, in Reexam Control No. U.S. Appl. No. 90/014,448 (10 pgs.).

(56) References Cited

OTHER PUBLICATIONS

Declaration of Prof Clive Wilson, filed in Opposition to European Patent No. 2 944 306 B1, executed Oct. 26, 2021 (75 pgs.).

Diehl et al., "A Good Practice Guide to the Administration of Substances and Removal of Blood, Including Routes and Volumes," *Journal of Applied Toxicology*, 21:15-23 (2001).

Drug Vehicle (Code C927), National Cancer Institute (NCI), retrieved Jan. 6, 2021, from <https://ncithesaurus.nci.nih.gov/ncitbrowser/ConceptReport jsp?dictionary=NCI_Thsaurus&ns=ncit&code=C927 >, as submitted to the USPTO on Jan. 7, 2021, in *Inter Partes* Review No. IPR2021-00402, 1 pg.

Drug Approval Package: Avastin (Bevacizum) NDA #125085, 2 pgs. (2005).

Drug Approval Package: Lucentis (Ranibizumab) Injection Company: Genetech, Inc. Application No. 12156, 2 pgs (2006).

Drug Approval Package: Macugen (Pegaptanib Sodium) Injection Company: Eyetech Pharmaceuticals, Inc. Application No. 021756, , 2 pgs. (2005).

ENBREL® Label (Revised Jul. 2005) (64 pgs.).

EYLEA® Product Insert (Revised Mar. 2021) (32 pgs.).

EYLEA® Product Insert (Revised Jul. 2021) (36 pgs.).

Excerpts from Antibody Fusion Proteins (S.M. Chamow & A. Ashkenazi (eds.) 221-309 (1999).

Fast et al., "Physical Instability of a Therapeutic Fc Fusion Protein: Domain Contributions to Conformational and Colloidal Stability," *Biochemistry*, 48(49):11724-11736 (2009).

Fransson et al., "Local Tolerance of Subcutaneous Injections," *J. Pharm. Pharmacol.*, 48:1012-1015 (1996).

Fraser et al., "Single Injections of Vascular Endothelial Growth Factor Trap Block Ovulation in the Macaque and Produced Prolonged, Dose-Related Suppression of Ovarian Function," *J. Clin. Endocrin. & Metabol.* 90(2):1114-1122 (2004).

Frenken et al., "Identification of the Component Part in an Epoetin Alfa Preparation That Causes Pain After Subcutaneous Injection," *American Journal of Kidney Diseases*, 22(4):553-556 (1993).

Frokjaer et al., "Pharmaceutical Formulation Development of Peptides and Proteins," Taylor & Francis, Philadelphia, PA, pp. 146-171 (2000).

Gasteiger et al., "ExPASy: the proteomics server for in-depth protein knowledge and analysis," *Nucleic Acids Research*, 31(13):3784-3788 (2003).

Glade-Blender et al., "VEFG Blocking Therapy in the Treatment of Cancer," *Expert Opinion on Biological Therapy*. Ashley London GB 3(2): 263-276 (Apr. 2003).

Gokarn et al., "Excipients for Protein Drugs," Excipient Development for Pharmaceutical, Biotechnology, and Drug Delivery Systems, 291-331 (2006).

Hanks Solution, http://www.lifetechnologies.com/us/en/home/technical-resources/media-formulation.152.html (1pg.).

Harris, "Processing of C-terminal lysine and arginine residues of proteins isolated from mammalian cell culture," *Journal of Chromatography A*, 705:129-134 (1995).

HERCEPTIN® label (Sep. 1998) (2 pgs.).

Hermosilla et al., "Comprehensive biophysical and functional study of ziv-aflibercept: characterization and forced degradation," *Scientific Reports*, 10(2675):1-13 (2020).

Hirvonen et al., "Hydrodynamic Radii of Ranibizumab, Aflibercept and Bevacizumab Measured by Time-Resolved Phosphorescence Anisotropy," *Pharm Res*, 33:2025-2032 (2016).

Holash et al., "VEGF-Trap: A VEGF blocker with potent antitumor effects," PNAS, 99(17):11393-11398 (2002).

Hossler et al., "Optimal and consistent protein glycosylation in mammalian cell culture," *Glycobiology*, 19(9):936-949 (2009).

Huang et al., "Regression of established tumors and metastases by potent vascular endothelial growth factor blockade," *PNAS*, 100(13):7785-7790 (2003).

ICH, Guidance for Industry: Q5C Quality of Biotechnological Products: Stability Testing of Biotechnological/Biological Products, 9 pgs. (Jul. 1996).

ICH, Guidance for Industry: Q6B Specifications: Test Procedures and Acceptance Criteria for Biotechnological/Biological Products, 17 pgs. (Sep. 1999).

Intraocular Product Information, Physician's Desk Reference for Ophthalmology, pp. 318-319 (1999).

Intravitreal VEGF Trap looking promising, p. 1 (Feb. 21, 2006) <https://europe.ophthalmologytimes.com/view/intravitreal-vegf-trap-looking-promising>.

Jaissle et al., "Intravitreal injections—High Standards of Procedure Necessary," *Klin Monatsbl Augenheilkd*, 222:389, 4 pgs. (2005) (with English language translation).

Janeway et al., "The structure of a typical antibody molecule," Immunobiology: The Immune System in Health and Disease, 5th edition, New York: Garland Science, 6 pgs. (2001).

Jefferis, "Glycosylation of Recombinant Antibody Therapeutics," *Biotechnol. Prog.*, 21:11-16 (2005).

Katayama et al., "Retrospective statistical analysis of lyophilized protein formulations of progenipoietin using PLS: determination of the critical parameters for long-term storage stability," *J. Pharm. Sci.*, 93(10): 2609-2623 (2004).

KEGG (Kyoto Encyclopedia of Genes and Genomes) Product Information Sheet for Aflibercept (1 pg.).

Kendrick et al., "Physical Stability of Proteins in Aqueous Solution," in *Rational Design of Stable Protein Formulations*, pp. 61-84, Kluwer Academic/Plenum publishers, New York, NY(2002).

Kerwin, "Polysorbates 20 and 80 Used in the Formulation of Protein Biotherapeutics: Structure and Degradation Pathways," *Journal of Pharmaceutical Sciences*, 97(8):2924-2935 (2008).

Kim et al., "Potent VEGF blockade causes regression of coopted vessels in a model of neuroblastoma," *PNAS*, 99(17):11399-11404 (2002).

Laursen et al., "Pain Perception after Subcutaneous Injections of Media Containing Different Buffers," *Basic & Clinical Pharmacology & Toxicology*, 98:218-221 (Jan. 2006).

Lopez et al., "Comparative enhancer effects of Span 20 with Tween 20 and Azone of the in vitro percutaneous penetration of compounds with different lipophilicites," *International Journal of Pharmaceutics*,202(1-2):133-140 (Jul. 1, 2000).

LUCENTIS® label (2006) (2 pgs.).

LUCENTIS® Label (2014) (14 pgs.).

Macugen® Label, NDA 21-756, pp. 4-11 (revised Jul. 2011).

Mi et al., "Effects of polyethylene glycol molecular weight and concentration on lactate dehydrogenase activity in solution and after freeze-thawing," *PDA J. Pharm. Sci. Technol.*, 56:115-123 (2002).

Moroney et al., "Aflibercept in epithelial ovarian carcinoma," *Future Oncol.*, 5(5):591-600 (2009).

Ng et al., "Pegaptanib, a targeted anti-VEGF aptamer for ocular vascular disease," *Nature Reviews*, 5:123-132 (Feb. 2006).

Ng et al., "Targeting angiogenesis, the underlying disorder in neovascular age-related macular degeneration," *Can J Ophthalmol*, 4(3):352-368 (2005).

Nguyen et al., "Results of a Phase I, Dose-Escalation, Safety, Tolerability, and Bioactivity Study of Intravitreous VEGF Trap in Patients With Neovascular Age-Related Macular Degeneration," *ARVO Annual Meeting Abstract*, pp. 1-2 (May 2006).

Order Granting Request for Ex Parte Reexamination dated Apr. 1, 2020, in Reexam Control No. U.S. Appl. No. 90/014,448 (21 pgs.).

Order Granting Unopposed Motions to Dismiss the Petition and Terminate the Proceeding Before Institution 37 C.F.R. §§ 42.5(a), 42.71(a) entered Jun. 25, 2021, in *Inter Partes* Review No. IPR2021-00402 (U.S. Pat. No. 10,464,992 B2)/PGR2021-00035 (U.S. Pat. No. 10,828,345 B2) (3 pgs.).

ORENCIA® Label (Mar. 2017) (30 pgs.).

Parkins et al., "The formulation of biopharmaceutical products," *Pharmaceutical Science & Technology Today*, 3(4):129-137 (2000).

Patent Owner's Mandatory Notices dated Jan. 25, 2021, in *Inter Partes* Review No. IPR2021-00402 (7 pgs.).

Petition for *Inter Partes* Review of U.S. Pat. No. 10,464,992 Under 35 U.S.C. §§ 311-319 and 37 C.F.R. § 42.100 et seq. (*Inter Partes* Review No. IPR2021-00402), executed Jan. 7, 2021 (59 pgs.).

Petition to Vacate *Ex Parte* Reexamination Order or, in the Alternative, to Stay Reexamination Proceeding Pursuant to 37 C.F.R. §§

(56) References Cited

OTHER PUBLICATIONS 1.181 and 1.182 in Reexam Control No. U.S. Appl. No. 90/014,448, executed May 29, 2020 (33 pgs.).
Petitioner's Unopposed Motion to Terminate Proceedings Pursuant to 35 U.S.C. § 317(A) dated Jun. 23, 2021, in *Inter Partes* Review No. IPR2021-00402 (5 Pgs-).
Preliminary Response of Patent Owner Regeneron Pharmaceuticals, Inc dated Apr. 14, 2021, in *Inter Partes* Review No. IPR2021-00402 (63 pgs.).
RAPTIVA® Label (Issued Mar. 2009) (36 pgs.).
Remington's Pharmaceutical Sciences, 18th Edition—Polysorbated (1990) (4 pgs.).
Request for *Ex Parte* Reexamination of U.S. Pat. No. 10,464,992 (Furfine et al.), filed Feb. 11, 2020 (78 pgs.).
Ribeiro et al., "An Algorithm for the Computer Calculation of the Coefficients of a Polynomial that Allows Determination of Isoelectric Points of Proteins and Other Macromolecules," *Comput. Biol. Med.*, 20(4):235-242 (1990).
Rich et al., "Short-Term Safety and Efficacy of Intravitreal Bevacizumab (Avastin) for Neovascular Age-Related Macular Degeneration," *Retina, The Journal of Retinal and Vitreous Diseases*, 26(5):495-511 (May 2006).
Riss et al., "Choosing the Right Cell-Based Assay for Your Research," *Cell Notes*, 6:6-12 (2003).
Riss et al., "Use of Multiple Assay Endpoints to Investigate the Effects of Incubation Time, Dose of Toxin, and Plating Density in Cell-Based Cytotoxicity Assays," *ASSAY and Drug Development Technologies*, 2(1):51-75 (2004).
Riss, "Selecting Cell-Based Assays for Drug Discovery Screening," *Cell Notes*, 13:16-21 (2005).
Rosenfeld, "An Update on Bevacizumab," *Review of Ophthalmology*, 1-5 (Jan. 2006).
Routier et al., "The glycosylation pattern of a humanized IgG1 antibody (D1.3) expressed in CHO cells," *Glycoconjugate J.*, 14:201-207 (1997).
Rudd et al., "Glycosylation: Heterogeneity and the 3D Structure of Proteins," *Critical Reviews in Biochemistry & Molecular Bio.*, 32(1):1-100 (1997).
Saishin et al., "VEGF-TRAP$_{R1R2}$ Suppresses Choroidal Neovascularization and VEGF-Induced Breakdown of the Blood-Retinal Barrier," *Journal of Cellular Physiology*, 195:241-248 (2003).
Securities Daily, Announcement of Chengdu Kanghong Pharmaceutical Group Co., Ltd. on stopping the global multi-center clinical trial of Conbercept ophthalmic injection (Apr. 13, 2021) (with English language machine translation), available at <http://epaper.zqrb.cn/html/2021-04/10/content_716426.htm?div=-1.>.
Shukla et al., "Downstream Processing of Fc-Fusion Proteins," *Therapeutic Fc-Fusion Proteins*, 97-114 (2014).
Shukla et al., "Protein aggregation kinetics during Protein A chromatography Case study for an Fc fusion protein," *Journal of Chromatography A*, 1171:22-28 (2007).
Souillac, "Biophysical Characterization of Insoluble Aggregates of a Multi-Domain Protein: An Insight into the Role of the Various Domains," *Journal of Pharmaceutical Sciences*, 94:2069-2083 (2005).
Stewart, "Clinical and differential utility of VEGF inhibitors in wet age-related macular degeneration: focus on aflibercept," *Clinical Ophthalmology*, 6; 175-1186 (2012).
Strickley, "Solubilizing Excipients in Oral and Injectable Formulations," *Pharmaceutical Research*, 21(2):201-230 (2004).
Tang, China's Kanghong Pharma Hits Limit Down as France Stops Trials of Ophthalmic Drug, YiCai Global (Mar. 29, 2021) https://www.yicaiglobal.com/news/china-kanghong-pharma-hits-limit-down-as-france-stops-trials-of-ophthalmic-drug.
Thorpe et al., "The Use of Bioassays for the Characterisation and Control of Biological Therapeutic Products Produced by Biotechnology," *Dev. Biol. Stand*, 91:79-88 (1997).
Van Slyke, "On the Measurement of Buffer Values and on the Relationship of Buffer Value to the Dissociation Constant of the Buffer and the Concentration and Reaction of the Buffer Solution," Hospital of The Rockefeller Institute for Medical Research, 525-570 (1922).
Voight, "Injection and infusion preparations," *Pharmazeutische Technologie*, 461-462 (2006) (with English language translation).
Wang et al., "Antibody Structure, Instability, and Formulation," *Journal of Pharmaceutical Sciences*, 96(1)1-26 (2007).
Wang et al., "Glycoengineering of CHO cells to improve product quality," Paula Meleady (ed.), Heterologous Protein Production in CHO Cells: Methods and Protocols, Methods in Molecular Biology, vol. 1603: 25-44, DOI 10.1007/978-1-4939-6972-2_2, © Springer Science+Buisness Media LLC (2017).
Wang, "Instability, stabilization, and formulation of liquid protein pharmaceuticals," *International Journal of Pharmaceutics*, 185:129-188 (1999).
Wang, "Protein aggregation and its inhibition in biopharmaceutics," *International Journal of Pharmaceutics*, 289:1-30 (2005).
Webb et al., "A new mechanism for decreasing aggregation of recombinant human interferon-gamma by a surfactant: slowed dissolution of lyophilized formulations in a solution containing 0.03% polysorbate 20," *J. Pharm. Sci*, 93(10): 2609-2623(2002).
White et al., "Best practices in bioassay development to support registration of biopharmaceuticals," *BioTechniques*, 67(3):126-137 (2019).
Winter et al., "Man-made antibodies," *Nature*, 349:293-299 (1991).
XOLAIR® Label (2003) (17 pgs.).
Andersen et al., "Recombinant protein expression for therapeutic applications," *Current Opinion in Biotechnology*, 13:117-123 (2002).
Anonymous: "Lucentis in the treatment of neovascular (wet) age-related macular degeneration (AMD)", Jan. 1, 2007, pp. 1-54.
AVASTIN® label, as submitted to the USPTO on Jan. 7, 2021, in *Inter Partes* Review No. IPR2021-00402, 37 pgs.
Bontempo, "Preformulation Development of Parenteral Biopharmaceuticals," *Drugs and the Pharmaceutical Sciences*, 85:91-108 (1997).
Certificate of Correction dated Mar. 3, 2020, in U.S. Pat. No. 10,464,992, 1 pg.
Chi et al., "Physical Stability of Proteins in Aqueous Solution: Mechanism and Driving Forces in Nonnative Protein Aggregation," *Pharmaceutical Research*, 20(9):1325-1336 (2003).
Controls in SCI experiments, RegenBase, retrieved Jan. 6, 2021, from <http://regenbase.org/control-groups.html>, as submitted to the USPTO on Jan. 7, 2021, in *Inter Partes* Review No. IPR2021-00402, 2 pgs.
Declaration of Dr. Reiner Gentz, as submitted to the USPTO on Jan. 7, 2021, in *Inter Partes* Review No. IPR2021-00402, 76 pgs.
Declaration Pursuant to 37 C.F.R. § 1.131 of Daniel B. Dix, Kelly Frye, and Susan Kautz in Support of Response to Office Action in U.S. Appl. No. 12/835,065, filed Nov. 22, 2011, as submitted to the USPTO on Jan. 7, 2021, in *Inter Partes* Review No. IPR2021-00402, 11 pgs.
Drug Vehicle (Code C927), National Cancer Institute (NCI), retrieved Jan. 6, 2021, from <https://ncithesaurus.nci.nih.gov/ncitbrowser/ConceptReport jsp?dictionary=NCI_Thesaurus&ns=ncit&code=C927 >, as submitted to the USPTO on Jan. 7, 2021, in *Inter Partes* Review No. IPR2021-00402, 2 pgs.
Ex Parte Request for Reexamination of U.S. Pat. No. 10,464,992, pp. 1-70, published Feb. 11, 2020.
File History of U.S. Pat. No. 10,464,992, as submitted to the USPTO on Jan. 7, 2021, in *Inter Partes* Review No. IPR2021-00402, 124 pgs.
Fraser, Hamis M., et al., "Single Injections of Vascular Endothelial Growth Factor Trap Block Ovulation in the Macaque and Produced Prolonged, Dose-Related Suppression of Ovarian Function," (2004) J. Clin. Endocrin. & Metabol. 90(2):1114-1122.
"Guidance for Industry Q1A(R2) Stability Testing of New Drug Substances and Products," U.S. Department of Health and Human Services, Food and Drug Administration, Rockville, MD, as submitted to the USPTO on Jan. 7, 2021, in *Inter Partes* Review No. IPR2021-00402, 25 pgs.
HERCEPTIN® label, as submitted to the USPTO on Jan. 7, 2021, in *Inter Partes* Review No. IPR2021-00402, 2 pgs.

(56) References Cited

OTHER PUBLICATIONS

LUCENTIS® label, as submitted to the USPTO on Jan. 7, 2021, in *Inter Partes* Review No. IPR2021-00402, 14 pgs.
Petition for *Inter Partes* Review of U.S. Pat. No. 10,464,992, as submitted to the USPTO on Jan. 7, 2021, in *Inter Partes* Review No. IPR2021-00402, 59 pgs.
"Phosphate buffer," Cold Spring Harbor Protocols, 2006:pdb.rec8543, as submitted to the USPTO on Jan. 7, 2021, in *Inter Partes* Review No. IPR2021-00402, 1 pg.
Randolph et al., "Surfactant-Protein Interactions," *Rational Design of Stable Protein Formulations*, pp. 159-175, Springer, Boston, MA (2002).
RAPTIVA® label, as submitted to the USPTO on Jan. 7, 2021, in *Inter Partes* Review No. IPR2021-00402, 36 pgs.
REMICADE® label, as submitted to the USPTO on Jan. 7, 2021, in *Inter Partes* Review No. IPR2021-00402, 58 pgs.
Response to Office Action in U.S. Appl. No. 12/835,065, filed Nov. 22, 2011, as submitted to the USPTO on Jan. 7, 2021, in *Inter Partes* Review No. IPR2021-00402, 4pgs.
Resume of Reiner Gentz, Ph.D., as submitted to the USPTO on Jan. 7, 2021, in *Inter Partes* Review No. IPR2021-00402, 3 pgs.
Rudge et al., "VEGF Trap as a Novel Antiangiogenic Treatment Currently in Clinical Trials for Cancer and Eye Diseases, and VelociGene®-based Discovery of the Next Generation of Angiogenesis Targets," *Cold Spring Harbor Symposia on Quantitative Biology*, 70:411-418 (2004).
SIMULECT® label, as submitted to the USPTO on Jan. 7, 2021, in *Inter Partes* Review No. IPR2021-00402, 7 pgs.
USPTO Communication on Ex Parte Reexamination of U.S. Pat. No. 10,464,992, pp. 1-12, published Apr. 1, 2020.
Wulff et al., "Prevention of Thecal Angiogenesis, Antral Follicular Growth, and Ovulation in the Primate by Treatment with Vascular Endothelial Growth Factor Trap R1R2," *Endocrinology*, 143(7):2797-2807 (2002).
XOLAIR® label, as submitted to the USPTO on Jan. 7, 2021, in *Inter Partes* Review No. IPR2021-00402, 17 pgs.
Amin et al., "Lyophilization of Polyethylene Glyvol Mixtures," *Journal of Pharmaceutical Sciences*, 93(9): pp. 2244-2249 (2004).
Andya et al., "Mechanisms of Aggregate Formations and Carbohydrate Excipient Stabilization of Lyophilized Humanized Monoclonal Antibody Formulations," *AAPS PharmSci*, 5(2): Article 10, pp. 1-11 (Apr. 2003).
Application for Extension Patent Term Under 35 U.S.C. § 156 filed Dec. 22, 2011, in U.S. Pat. No. 7,374,758 (198 pgs.).
ARANESP® Prescribing Information (Revised Jun. 2011) (41 pgs.).
Atkinson et al., "Formulation Strategies for Biopharmaceuticals Enduring Success to Market," *The Investigational Drugs Journal*, 4(5): pp. 557-560 (2001).
Avastin® (Bevacizum) Drug Approval Package, NDA #12508, https://www.accessdate.fda.gov/drugatfda_docs/nda/2004/STN-125085_Avastin.cfm, 2 pp. (created Mar. 8, 2005).
Chang et al., "Practical Approaches to Protein Formulation Development," in *Rational Design of Stable Protein Formulations—Theory and Practice* (J.F. Carpenter and M.C. Manning eds.), Kluwer Academic/Plenum pubs. (NY), pp. 1-25 (2002).
Cleland et al., "The Development of Stable Protein Formulations: A Close Look at Protein Aggregation, Deamidation, and Oxidation," *Critical Reviews in Therapeutic Drug Carrier Systems*, 10(4): pp. 307-377 (1993).
Declaration in Support of Request for Ex Parte Reexamination of U.S. Pat. No. 10,406,226 (Dix et al.) by Steven M. Chamow, Ph.D. executed Feb. 5, 2020.
Declaration of Dr. Ralph Tarantino in Support of Petition for Post Grant Review of U.S. Pat. No. 10,857,231, executed Sep. 7, 2021 (236 pgs.).
Declaration of Rachel J. Watters, submitted in Petition for Post Grant Review of U.S. Pat. No. 10,857,231, executed Sep. 3, 2021 (21 pgs.).

*Development and Manufacture of Protein Pharmaceuticals*, Steven L. Nail and Michael J. Akers (eds.), Pharmaceutical Biotechnology, vol. 14, DOI 10.1007/978-1-4615-0546-5, Springer+Business Media New York (2002).
Disclaimer in Patent Under 37 C.F.R. § 1.321(a) of Frank R. Cottingham, Ph.D., J.D., in U.S. Pat. No. 10,857,231, executed Mar. 14, 2022 (1 pg.).
Dunleavy, "Special Reports: Humira," Fiercepharma (May 3, 2021) <https://www.fiercepharma.com/special-report/top-20-drugs-by2020-sales-humira> (Accessed on Nov. 19, 2021).
EPOGEN® Prescribing Information (Revised Sep. 2017) (59 pgs.).
European Search Report dated Aug. 4, 2011, in EP Application 11157965.
European Search Report dated Aug. 12, 2015 in EP Application 15169936.
European Search Report dated Nov. 12, 2020, in EP Application 20178021.
European Search Report dated Feb. 28, 2023, in EP Application 13152402.
Expert Declaration of Dr. Peter Tessier in Support of Petition for *Inter Partes* Review of U.S. Patent No. 10,406,226, dated Feb. 23, 2013, in IPR2023-00620 (60 pgs.).
Expert Declaration of Dr. Ralph Tarantino in Support of Petition for *Inter Partes* Review of U.S. Patent No. 10,464,992, filed Jan. 17, 2023, in IPR2023-00462 (85 pgs.).
EYLEA® Product Insert (Revised Feb. 2023) (40 pp.).
Fahrner et al., "Industrial Purification of Pharmaceutical Antibodies: Development, Operation, and Validation of Chromatography Processes," *Biotechnology and Genetic Engineering Reviews*, 18(1):pp. 301-327 (Jul. 2001).
Ferrara et al., "Angiogenesis as a therapeutic target," *Nature*, 438: pp. 967-974 (Dec. 2005).
File History of U.S. Appl. No. 16/535,610, filed Aug. 8, 2019, which issued as U.S. Pat. No. 10,857,231 on Dec. 8, 2020 (283 pgs.).
Gonal-F® Prescribing Information (Revised Dec. 2020) (33 pgs.).
HERCEPTIN®, *Physician's Desk Reference*, 59th Ed., Thompson PDR (NJ), pp. 313 & 1337-1341 (2005).
HUMALOG® Prescribing Information (Mar. 2013) (27 pgs.) Herewith.
HUMIRA™ Label (Dec. 20, 2002) (17 pgs.).
INFERGEN® Prescribing Information (Revised Jul. 2010) (39 pgs.).
International Preliminary Report on Patentability dated Sep. 25, 2007, for International Application PCT/US2006/010600.
International Search Report dated Sep. 19, 2006, for International Appln. PCT/US2006/010600.
International Search Report, dated Apr. 3, 2008, in International Appln. PCT/US2007/014085.
INTRON® a Prescribing Information (Revised Nov. 1997) (37 pgs.).
Ionescu et al., "Contribution of Variable Domains to the Stability of Humanized IgG1 Monoclonal Antibodies," *J. Pharm. Sci.*, 97(4):1414-1426 (Apr. 2008).
IPR2023-00462, Paper 2, Petition for *Inter Partes* Review of U.S. Pat. No. 10,464,992 (77 pgs.) (Jan. 17, 2023).
IPR2023-00620, Paper 2, Petition for *Inter Partes* Review of U.S. Patent No. 10,406,226 (75 pgs.).
Kalantar-Zadeh, "History of Erythropoiesis-Stimulating Agents, the Development of Biosimilars, and the Future of Anemia Treatment in Nephrology," *American Journal of Nephrology*, 45: pp. 235-247 (2017).
KINERET® Prescribing Information (Revised Dec. 2020) (18 pgs.).
Kostanski et al., "Size-exclusion chromatography—a review of calibration methodologies," *J. Biochem. Biophys. Methods*, 58: pp. 159-186 (2004).
Krapp et al., "Structural Analysis of Human IgG-Fc Glycoforms Reveals a Correlation Between Glycosylation and Structural Integrity," *Journal of Molecular Biology*, 325(5):pp. 979-989 (2003).
Krishnan et al., "Development of Formulations for Therapeutic Monoclonal Antibodies and Fc Fusion Proteins," in *Formulation*

(56) References Cited

OTHER PUBLICATIONS

*and Process Development Strategies for Manufacturing Biopharmaceuticals*, pp. 383-427, John Wiley & Sons, Inc., New Jersey, NY (2010).
Liu, "Antibody Glycosylation and Its Impact on the Pharmacokinetics and Pharmacodynamics of Monoclonal Antibodies and Fc-Fusion Proteins," *Journal of Pharmaceutical Sciences*, 104:pp. 1866-1884 (Apr. 14, 2015).
Macugen® (Pegaptanib Sodium) Injection Drug Approval Package, FDA database, NDA #021756, 2 pp. (created Mar. 23, 2005).
Malingre et al., "The Co-Solvent Cremophor EL Limits Absorption of Orally Administered Paclitaxel in Cancer Patients," *British Journal of Cancer*, 85(10): pp. 1472-1477 (2001).
McGoff et al., "Solution Formulation of Proteins/Peptides," in *Drugs and the Pharmaceutical Sciences, vol. 99: Protein Formulation and Delivery*(E.J. McNally ed.), Marcel Dekker, Inc. pub. (NY), pp. 139-158 (2000).
Mimura et al., "The role of oligosaccharide residues of IgG1-Fc in FcγIIb binding," *Journal of Biological Chemistry*, 276(49):45539-45547 (Sep. 20, 2001).
Molecular Approaches to Controlling Cancer, Cold Spring Harbor Symposia on Quantitative Biology, vol. LXX, pp. xxvii-xxix (2005).
NOVOLOG® Prescribing Information (Revised Feb. 2015) (51 pgs.).
NUTROPIN AQ® Prescribing Information (Revised Dec. 2016) (23 pgs.).
Opposition to Patent Owner's Petition to Vacate *Ex Parte* Reexamination Order or, in the Alternative, to Stay Reexamination Proceeding Pursuant to 37 C.F.R. §§ 1.181 and 1.182 in U.S. Appl. No. 90/014,448, executed Jun. 12, 2020 (53 pgs.).
Order Denying Institution of Post-Grant Review Pursuant to 35 U.S.C. § 324, entered Mar. 15, 2022, in Case PGR2021-00117 (U.S. Patent No. 10,857,231) (4 pgs.).
Order Granting Request for *Ex Parte* Reexamination dated Apr. 1, 2020, in Reexam Control No. 90/014,448 (21 pgs.).
Park Press Release, "Nucala 40mg Prefilled Syringe Approved for Children With Severe Eosinophilic Asthma," (Jan. 25, 2022).
Patent Owner Regeneron Pharmaceuticals, Inc.'s Sur-Reply to Petitioner's Reply to Patent Owner Preliminary Response, filed Jan. 25, 2022, in Case PGR2021-00117 (U.S. Pat. No. 10,857,231) (14 pgs.) (later withdrawn by the PTAB).
Patent Owner Regeneron Pharmaceuticals, Inc.'s Unopposed Motion to Withdraw Patent Owner's Preliminary Response and Surreply, filed Mar. 3, 2022, in Case PGR2021-00117 (U.S. Pat. No. 10,857,231) (4 pgs.).
Patro et al., "Protein Formulation and Fill-Finish Operations," *Biotechnology Annual Review*, 8:55-84 (2002).
Petition for Post-Grant Review of U.S. Pat. No. 10,857,231 Under 35 U.S.C. §§ 321-329 and 37 C.F.R. § 42.200 et seq. (Case PGR2021-00117), executed Sep. 7, 2021 (103 pgs.).
Petitioner's Reply to Patent Owner's Preliminary Response, filed Jan. 18, 2022, in Case PGR2021-00117 (U.S. Pat. No. 10,857,231) (16 pgs.).
Pre-filled Syringe, Collins Dictionary, https://www.collinsdictionary.com/de/worterbuch/englisch/pre-filled-syringe.
Preliminary Response of Patent Owner Regeneron Pharmaceuticals, Inc. filed Dec. 15, 2021, in Case PGR2021-00117 (U.S. Pat. No. 10,857,231) (92 pgs.) (later withdrawn by the PTAB).
Press Release, Novartis receives FDA approval of Xolair® (omalizumab self-injection with prefilled syringe across all indications for appropriate patients, (Apr. 12, 2021).
Press Release, Regeneron Reports Fourth Quarter and Full Year 2022 Financial and Operating Results (Feb. 3, 2023).
RAPTIVA®, *Physician's Desk Reference*, 59th Ed., Thompson Pdr (NJ), pp. 1350-1354 (2005).
*Rational Design of Stable Protein Formulations: Theory and Practice*, John F. Carpenter and Mark C. Manning (eds.), Pharmaceutical Biotechnology, vol. 13, DOI 10.1007/978-1-4615-0557-0, Springer Science+Business Media New York (2002).
REMICADE®, *Physician's Desk Reference*, 59th Ed., Thompson PDR (NJ),111 pp. 1117-1122 (2005).
Request for *Ex Parte* Reexamination of U.S. Pat. No. 10,406,226 (Dix et al.), filed Feb. 11, 2020 (90 pgs.).
Reply of Patentee in Opposition of EP 2944306 (Mar. 20, 2023).
SIMULECT®, *Physician's Desk Reference*, 59th Ed., Thompson PDR (NJ), pp. 325 & 2367-2369 (2005).
U.S. Food & Drug Administration, "Guidance for Industry—Container Closure Systems for Packaging Human Drugs and Biologics," (56 pgs.) (May 1999), submitted in IPR2023-00462 as Exhibit 1038.
U.S. Food & Drug Administration, "Guidance for Industry—Q6B Specification: Test Procedures and Acceptance Criteria for Biotechnological/Biological Products," (24 pgs.) (Aug. 1999), submitted in IPR2023-00462 as Exhibit 1047.
U.S. Food & Drug Administration, "Points to Consider in the Manufacture and Testing of Monoclonal Antibody Products for Human Use," pp. 1-50 (Feb. 28, 1997), submitted in IPR2023-00620 as Exhibit 1020.
van Bruggen et al., "VEGF antagonism reduces edema formation and tissue damage after ischemia/reperfusion injury in the mouse brain," *The Journal of Clinical Investigation*, 104(11): pp. 1613-1620 (1999).
Wang, "Lyophilization and Development of Solid Protein Pharmaceuticals," *International Journal of Pharmaceutics*, 203: pp. 1-60 (2000).
Wurm, "Production of Recombinant Protein Therapeutics in Cultivated Mammalian Cells," *Nature Biotechnology*, 22(11): pp. 1393-1398 (Nov. 2004).
XOLAIR®, Physician's Desk Reference, 59th Ed., Thompson PDR (NJ), pp. 1359-1362 (2005).
Zaltrap® (ziv-aflibercept), FDA Marketing Information, Initial U.S. Approval 2012, 17 pp.
Zhao et al., "Increasing the homogeneity, stability and activity of human serum albumin and interferon-α2b fusion protein by linker engineering," Protein Expression and Purification, 61:73-77 (2008).

VEGF ANTAGONIST FORMULATIONS SUITABLE FOR INTRAVITREAL ADMINISTRATION

CROSS-REFERENCE TO RELATED APPLICATIONS

This application is a continuation application of U.S. patent application Ser. No. 16/582,486 filed Sep. 25, 2019, which issued as U.S. Pat. No. 11,066,458 on Jul. 20, 2021, which is a continuation of U.S. patent application Ser. No. 16/159,269 filed Oct. 12, 2018, which issued as U.S. Pat. No. 10,464,992 on Nov. 5, 2019, which is a continuation of U.S. patent application Ser. No. 15/879,294 filed Jan. 24, 2018, which issued as U.S. Pat. No. 10,400,025 on Sep. 3, 2019, which is a continuation of U.S. patent application Ser. No. 15/095,606 filed Apr. 11, 2016, which issued as U.S. Pat. No. 9,914,763 on Mar. 13, 2018, which is a continuation of U.S. patent application Ser. No. 14/330,096, filed Jul. 14, 2014, which issued as U.S. Pat. No. 9,340,594 on May 17, 2016, which is a continuation of U.S. patent application Ser. No. 13/914,996, filed Jun. 11, 2013, which issued as U.S. Pat. No. 8,802,107 on Aug. 12, 2014, which is a continuation application of U.S. patent application Ser. No. 13/329,770, filed Dec. 19, 2011, which issued as U.S. Pat. No. 8,481,046 on Jul. 9, 2013, which is a continuation application of U.S. patent application Ser. No. 12/833,417, filed Jul. 9, 2010, which issued as U.S. Pat. No. 8,092,803 on Jan. 10, 2012, which is a continuation application of U.S. patent application Ser. No. 12/560,885, filed Sep. 16, 2009, which issued as U.S. Pat. No. 7,807,164 on Oct. 5, 2010, which is a divisional application of U.S. patent application Ser. No. 11/818,463, filed Jun. 14, 2007, which issued as U.S. Pat. No. 7,608,261 on Oct. 27, 2009, which claims the benefit under 35 U.S.C. § 119(e) of U.S. Provisional Application No. 60/814,484, filed Jun. 16, 2006, which applications are each hereby incorporated by reference.

BACKGROUND OF INVENTION

Field of the Invention

The present invention is directed to pharmaceutical formulations suitable for intravitreal administration comprising agents capable of inhibiting vascular endothelial growth factor (VEGF), and to methods for making and using such formulations. The invention includes liquid pharmaceutical formulations having increased stability, as well as formulations that may be lyophilize and reconstituted for intravitreal administration.

Statement of Related Art

Vascular endothelial growth factor (VEGF) expression is nearly ubiquitous in human cancer, consistent with its role as a key mediator of tumor neoangiogenesis. Blockade of VEGF function, by binding to the molecule or its VEGFR-2 receptor, inhibits growth of implanted tumor cells in multiple different xenograft models (see, for example, Gerber et al. (2000) Cancer Res. 60:6253-6258). A soluble VEGF-specific fusion protein antagonist, termed a "VEGF trap" has been described (Kim et al. (2002) Proc. Natl. Acad. Sci. USA 99:11399-404; Holash et al. (2002) Proc. Natl. Acad. Sci. USA 99:11393-8), which applications are specifically incorporated by reference in their entirety.

Ophthalmic formulations are known, see for example, U.S. Pat. Nos. 7,033,604 and 6,777,429. An ophthalmic formulation of a VEGF antibody is described in U.S. Pat. No. 6,676,941.

Lyophilization (freeze drying under controlled conditions) is commonly used for long-term storage of proteins. The lyophilized protein is substantially resistant to degradation, aggregation, oxidation, and other degenerative processes while in the freeze-dried state (see, for example, U.S. Pat. No. 6,436,897).

BRIEF SUMMARY OF THE INVENTION

Stable formulations of a VEGF-specific fusion protein antagonist are provided. Pharmaceutically acceptable formulations are provided that comprise a VEGF "trap" antagonist with a pharmaceutically acceptable carrier. In specific embodiments, liquid and lyophilized formulations are provided.

In a first aspect, a stable liquid ophthalmic formulation of a VEGF-specific fusion protein antagonist is provided, comprising a fusion protein that comprises a receptor component consisting essentially of an immunoglobulin-like (Ig) domain 2 of a first VEGF receptor and Ig domain 3 of a second VEGF receptor, and a multimerizing component (also termed a "VEGF trap"). In a specific embodiment of the VEGF-specific fusion protein antagonist, the first VEGF receptor is Flt1 and the second VEGF receptor is Flk1 or Flt4. In a more specific embodiment the fusion protein has the amino acid sequence of SEQ ID NO:2 or SEQ ID NO:4. Preferably, the VEGF antagonist is a dimer comprising two fusion proteins of SEQ ID NO:4.

In one aspect, a stable liquid ophthalmic formulation is provided that comprises 1-100 mg/ml VEGF-specific fusion protein antagonist, 0.01-5% of one or more organic co-solvent(s), 30-150 mM of one or more tonicity agent(s), 5-40 mM of a buffering agent, and optionally, 1.0-7.5% of a stabilizing agent, pH between about 5.8-7.0.

In one or more specific embodiments, the organic co-solvent may be polysorbate, for example, polysorbate 20 or polysorbate 80, polyethylene glycol (PEG), for example, PEG 3350, or propylene glycol, or a combination thereof; the tonicity agent may be, for example, sodium chloride or potassium chloride; the stabilizing agent may be sucrose, sorbitol, glycerol, trehalose, or mannitol; and the buffering agent may be, for example, phosphate buffer. In a specific embodiment, the phosphate buffer is a sodium phosphate buffer.

In various embodiments, the organic co-solvent is polysorbate and/or PEG, the stabilizing agent is sucrose, the buffering agent is phosphate buffer, and the tonicity agent is sodium chloride.

More specifically, the stable liquid ophthalmic formulation comprises about 40-50 mg/ml of the VEGF antagonist (SEQ ID NO:4), about 10 mM phosphate buffer, 0.01-3% polysorbate and/or PEG, 40-135 mM sodium chloride, and optionally 5.0% sucrose, pH about 6.2-6.3.

In a specific preferred embodiment, the stable liquid ophthalmic formulation comprises about 50 mg/ml of the VEGF antagonist (SEQ ID NO:4), 10 mM sodium phosphate buffer, 50 mM sodium chloride, 0.1% polysorbate, and 5% sucrose, pH about 6.2-6.3.

In a specific preferred embodiment, the stable liquid ophthalmic formulation comprises about 50 mg/ml of the VEGF antagonist (SEQ ID NO:4), 10 mM sodium phosphate buffer, 50 mM sodium chloride, 3% PEG, and 5% sucrose, pH about 6.2-6.3.

In a specific preferred embodiment, the stable liquid ophthalmic formulation comprises about 40 mg/ml of the VEGF antagonist (SEQ ID NO:4), 10 mM sodium phosphate buffer, 40 mM sodium chloride, 0.03% polysorbate, and 5% sucrose, pH about 6.2-6.3.

In a specific preferred embodiment, the stable liquid ophthalmic formulation comprises about 40 mg/ml of the VEGF antagonist (SEQ ID NO:4), 10 mM sodium phosphate buffer, 135 mM sodium chloride, and 0.03% polysorbate, pH about 6.2-6.3.

In another aspect, a stable liquid ophthalmic formulation is provided that comprises 1-100 mg/ml VEGF-specific fusion protein antagonist; 0.01-5% of one or more organic co-solvent(s); 5-40 mM of a buffering agent; and optionally 30-150 mM of one or more tonicity agent(s) and/or 1.0-7.5% of a stabilizing agent; having a pH between about 5.8-7.0.

In various embodiments, the VEGF antagonist (SEQ ID NO:4) is present at a concentration of about 10 to about 80 mg/ml. In various embodiments, the VEGF antagonist (SEQ ID NO:4) is present at a concentration of about 10, about 20, about 30, about 40, about 50, about 60, about 70, or about 80 mg/ml. In a preferred embodiment, the VEGF antagonist (SEQ ID NO:4) is present at a concentration of about 40 mg/ml.

In another embodiment, the stabilizing agent is selected from one or more of sucrose, sorbitol, glycerol, trehalose, and mannitol.

In another embodiment, the organic co-solvent is selected from one or more of polysorbate, for example, polysorbate 20 or polysorbate 80, polyethylene glycol (PEG), for example, PEG 3350, and propylene glycol.

In another embodiment, the buffer is a phosphate buffer, for example, sodium phosphate.

In another embodiment, the tonicity agent is a salt, for example, sodium chloride.

In one embodiment, the stable liquid ophthalmic formulation comprises 10 mM sodium phosphate buffer, about 0.03 to about 0.1% polysorbate and/or about 3% PEG or propylene glycol, about 40 mM sodium chloride, and about 5% sucrose. In a specific embodiment, the stable liquid ophthalmic formulation comprises 10 mM sodium phosphate buffer, about 0.03% polysorbate, about 40 mM sodium chloride, and about 5% sucrose. In another specific embodiment, the pH of the formulation is about 6.2 to about 6.3. In another specific embodiment, the pH is achieved by mixing mono- and dibasic sodium phosphate to the desired pH without acid/base titration.

In a specific embodiment, the stable liquid ophthalmic formulation consists essentially of a VEGF antagonist (SEQ ID NO:4) at 40 mg/ml, 10 mM sodium phosphate buffer, polysorbate at 0.03%, sodium chloride at 40 mM, and sucrose at 5%, pH 6.2-6.3.

In another aspect, a stable liquid ophthalmic formulation is provided that comprises about 10 to about 80 mg/ml VEGF antagonist, about 10 mM sodium phosphate buffer, about 0.03% polysorbate, and about 135 mM sodium chloride, pH 6.2 to 6.3.

In various embodiments, the VEGF antagonist (SEQ ID NO:4) is present at a concentration of about 10 to about 80 mg/ml. In various embodiments, the VEGF antagonist (SEQ ID NO:4) is present at a concentration of about 10, about 20, about 30, about 40, about 50, about 60, about 70, or about 80 mg/ml. In a specific embodiment, the VEGF antagonist (SEQ ID NO:4) is present at a concentration of about 40 mg/ml.

In one embodiment, the stable liquid ophthalmic formulation comprises 40 mg/ml of VEGF antagonist (SEQ ID NO:4), 10 mM sodium phosphate buffer, 0.03% polysorbate, and 135 mM sodium chloride at pH 6.2-6.3. In a specific embodiment, the stable liquid ophthalmic formulation consists essentially of 40 mg/ml of VEGF antagonist (SEQ ID NO:4), 10 mM sodium phosphate buffer, 0.03% polysorbate, and 135 mM sodium chloride at pH 6.2-6.3.

In another aspect, a lyophilizable formulation of a VEGF antagonist is provided, wherein upon lyophilization followed by reconstitution, a stable liquid ophthalmic formulation as described herein is obtained.

In another aspect, a lyophilizable formulation of a vascular endothelial growth factor (VEGF)-specific fusion protein antagonist is provided, comprising 5-50 mg/ml of the VEGF antagonist, 5-25 mM buffer, such as phosphate buffer, 0.01 to 0.15% of one or more of an organic co-solvent, such as polysorbate, propylene glycol and/or PEG, and optionally 1-10% of a stabilizing agent such as sucrose, sorbitol, trehalose, glycerol, or mannitol, pH about 5.8-7.0. In various embodiments, the VEGF antagonist (SEQ ID NO:4) is present at about 5, about 10, about 20, about 30, or about 40 mg/ml. In a specific embodiment, the lyophilizable ophthalmic formulation of the invention comprises 20 mg/ml of the VEGF antagonist, 10 mM sodium phosphate buffer, 0.03% polysorbate, 0.1% PEG, and 2.5% sucrose, pH about 6.2-6.3. In further embodiments, the lyophilizable formulation further comprises sodium chloride. In a specific embodiment, the sodium chloride is present at a concentration of about 20 mM. In another specific embodiment, the sodium chloride is present at a concentration of about 67.5 mM.

In another specific embodiment, the lyophilizable ophthalmic formulation of the invention comprises 20 mg/ml of the VEGF antagonist, 5 mM sodium phosphate buffer, 0.015% polysorbate, 20 mM sodium chloride, and 2.5% sucrose, pH about 6.2-6.3.

In another embodiment, the lyophilizable ophthalmic formulation comprises 5 mg/ml, 10 mg/ml, or 40 mg/ml VEGF antagonist, 5 mM sodium phosphate buffer, 0.015% polysorbate, 20 mM sodium chloride, and 2.5% sucrose, at pH 6.2-6.3. In a specific embodiment, the lyophilizable ophthalmic formulation consists essentially of 5 mg/ml, 10 mg/ml, or 40 mg/ml VEGF antagonist (SEQ ID NO:4), 5 mM sodium phosphate buffer, 0.015% polysorbate, 20 mM sodium chloride, and 2.5% sucrose, at pH 6.2-6.3.

In another embodiment, the lyophilizable ophthalmic formulation comprises 20 mg/ml of the VEGF antagonist, 5 mM sodium phosphate buffer, 0.015% polysorbate, and 67.5 mM sodium chloride, pH about 6.2-6.3. In a more specific embodiment, the lyophilizable ophthalmic formulation consists essentially of 20 mg/ml of the VEGF antagonist (SEQ ID NO:4), 5 mM sodium phosphate buffer, 0.015% polysorbate, and 67.5 mM sodium chloride, pH 6.2-6.3.

In another specific embodiment, the lyophilizable ophthalmic formulation comprises 5 mg/ml, 10 mg/ml, or 40 mg/ml VEGF antagonist, 5 mM sodium phosphate buffer, 0.015% polysorbate, and 67.5 mM sodium chloride, pH about 6.2-6.3. In a more specific embodiment, the lyophilizable ophthalmic formulation consists essentially of 5 mg/ml, 10 mg/ml, or 40 mg/ml VEGF antagonist (SEQ ID NO:4), 5 mM sodium phosphate buffer, 0.015% polysorbate, and 67.5 mM sodium chloride, pH about 6.2-6.3.

Generally, the reconstituted formulation is about 2 times the concentration of the pre-lyophilized formulation, e.g., a 20 mg fusion protein/ml pre-lyophilized formulation is reconstituted to a final formulation of 40 mg fusion protein/ml.

Generally, the lyophilized formulation is reconstituted with sterile water suitable for injection. In one embodiment, the reconstitution liquid is bacteriostatic water.

In another aspect, the invention features a method of producing a lyophilized formulation of a VEGF-specific fusion protein antagonist, comprising subjecting the lyophilizable formulation of the invention to lyophilization to generate a lyophilized formulation. The lyophilized formulation may be lyophilized by any method known in the art for lyophilizing a liquid.

In another related aspect, the invention features a method of producing a reconstituted lyophilized formulation of a VEGF antagonist, comprising reconstituting the lyophilized formulation of the invention to a reconstituted formulation. In one embodiment, the reconstituted formulation is twice the concentration of the pre-lyophilized formulation, e.g., the method of the invention comprises: (a) producing a pre-lyophilized formulation of a VEGF-specific fusion protein antagonist, (b) subjecting the pre-lyophilized formulation of step (a) to lyophilization; and (c) reconstituting the lyophilized formulation of step (b).

The invention further features ophthalmic formulations provided in a pre-filled syringe or vial, particularly suitable for intravitreal administration.

Other objects and advantages will become apparent from a review of the ensuing detailed description.

DETAILED DESCRIPTION OF THE INVENTION

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

Unless stated otherwise, all technical and scientific terms and phrases used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference.

General Description

Safe handling and administration of formulations comprising proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation and/or precipitation.

Chemical and physical stability can be promoted by removing water from the protein. Lyophilization (freeze-drying under controlled conditions) is commonly used for long-term storage of proteins. The lyophilized protein is substantially resistant to degradation, aggregation, oxidation, and other degenerative processes while in the freeze-dried state. The lyophilized protein may be reconstituted with water optionally containing a bacteriostatic preservative (e.g., benzyl alcohol) prior to administration.

Definitions

The term "carrier" includes a diluent, adjuvant, excipient, or vehicle with which a composition is administered. Carriers can include sterile liquids, such as, for example, water and oils, including oils of petroleum, animal, vegetable or synthetic origin, such as, for example, peanut oil, soybean oil, mineral oil, sesame oil and the like.

The term "excipient" includes a non-therapeutic agent added to a pharmaceutical composition to provide a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "lyophilized" or "freeze-dried" includes a state of a substance that has been subjected to a drying procedure such as lyophilization, where at least 90% of moisture has been removed.

VEGF Antagonists

A VEGF antagonist is a compound capable of blocking or inhibiting the biological action of vascular endothelial growth factor (VEGF), and includes fusion proteins capable of trapping VEGF. In a preferred embodiment, the VEGF antagonist is the fusion protein of SEQ ID NO:2 or 4; more preferably, SEQ ID NO:4. In specific embodiments, the VEGF antagonist is expressed in a mammalian cell line such as a CHO cell and may be modified post-translationally. In a specific embodiment, the fusion protein comprises amino acids 27-457 of SEQ ID NO:4 and is glycosylated at Asn residues 62, 94, 149, 222 and 308. Preferably, the VEGF antagonist is a dimer composed of two fusion proteins of SEQ ID NO:4.

The VEGF antagonist of the methods and formulations of the invention can be prepared by any suitable method known in the art, or that comes to be known. The VEGF antagonist is preferably substantially free of protein contaminants at the time it is used to prepare the pharmaceutically acceptable formulation. By "substantially free of protein contaminants" is meant, preferably, that at least 90% of the weight of protein of the VEGF-specific fusion protein antagonist preparation used for making a formulation is VEGF fusion protein antagonist protein, more preferably at least 95%, most preferably at least 99%. The fusion protein is preferably substantially free of aggregates. "Substantially free of aggregates" means that at least 90% of the weight of fusion protein is not present in an aggregate at the time the fusion protein is used to prepare the pharmaceutically effective formulation. Unless stated otherwise, the phosphates employed are sodium phosphates and a desired buffering pH is achieved by mixing appropriate amounts of mono- and dibasic sodium phosphate.

Stable Liquid Ophthalmic Formulations

In one aspect, the invention provides a stable pharmaceutically acceptable formulation comprising a VEGF antagonist, wherein the formulation is a liquid formulation suitable for ophthalmic use. Preferably, the liquid formulation comprises a pharmaceutically effective amount of the VEGF antagonist. The formulation can also comprise one or more pharmaceutically acceptable carriers, buffers, tonicity agents, stabilizers, and/or excipients. An example of a pharmaceutically acceptable liquid formulation comprises a VEGF antagonist in a pharmaceutically effective amount, a buffer, an organic co-solvent such as polysorbate, a tonicity agent such as NaCl, and optionally, a stabilizer such as sucrose or trehalose.

Stability is determined in a number of ways at specified time points, including determination of pH, visual inspection of color and appearance, determination of total protein content by methods known in the art, e.g., UV spectroscopy, and purity is determined by, for example, SDS-PAGE, size-exclusion HPLC, bioassay determination of activity, isoelectric focusing, and isoaspartate quantification. In one example of a bioassay useful for determining VEGF antagonist activity, a BAF/3 VEGFR1/EPOR cell line is used to determine VEGF165 binding by the VEGF antagonist of the invention.

Liquid formulations can be stored in an oxygen-deprived environment. Oxygen-deprived environments can be generated by storing the formulations under an inert gas such as, for example, nitrogen or argon. Liquid formulations are preferably stored at about 5° C.

Ophthalmic Lyophilized Formulations

In one aspect of the invention, an ophthalmically acceptable formulation comprising a VEGF antagonist is provided, wherein the formulation is a lyophilizable formulation. Lyophilizable formulations can be reconstituted into solutions, suspensions, emulsions, or any other suitable form for administration or use. Lyophilizable formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored below 25° C., for example, refrigerated at 2-8° C., or at room temperature (e.g., approximately 25° C.). Preferably, lyophilized formulations are stored below about 25° C., more preferably, at about 4-20° C.; below about 4° C.; below about −20° C.; about −40° C.; about −70° C., or about −80° C. Stability of the lyophilized formulation may be determined in a number of ways known to the art, for example, by visual appearance of the cake and/or by moisture content.

Lyophilized formulations are typically reconstituted for use by addition of an aqueous solution to dissolve the lyophilized formulation. A wide variety of aqueous solutions can be used to reconstitute a lyophilized formulation. Preferably, lyophilized formulations are reconstituted using water. Lyophilized formulations are preferably reconstituted with a solution consisting essentially of water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used.

Freeze-dried or lyophilized formulations are typically prepared from liquids, that is, from solutions, suspensions, emulsions, and the like. Thus, the liquid that is to undergo freeze-drying or lyophilization preferably comprises all components desired in a final reconstituted liquid formulation. As a result, when reconstituted, the freeze-dried or lyophilized formulation will render a desired liquid formulation upon reconstitution.

EXAMPLES

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only to the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Example 1. Stability of 50 mg/ml VEGF Trap Liquid Formulation Stored at 5° C. in 3 ml Glass Vials An ophthalmic liquid formulation containing 50 mg/ml VEGF Trap (SEQ ID NO:4), 10 mM phosphate, 50 mM NaCl, 0.1% polysorbate 20, 5% sucrose, and pH 6.25, was stored at 5° C. in 3 ml glass vials and samples tested at 3, 6, 9, 12, 18 and 24 months. Stability was determined by SE-HPLC. The results are shown in Table 1. Turbidity was measured at $OD_{405}$ nm; and percent recovered protein and purity by size exclusion HPLC.

TABLE 1

Stability of 50 mg/ml VEGF Trap Protein (VGFT-SS065)

| Months | Visual Appearance | Turbidity ($OD_{405}$ nm) | pH | % VEGF Trap Recovered | % VEGF Trap Native Configuration |
|---|---|---|---|---|---|
| 0 | Pass | 0.00 | 6.2 | 100 | 98.8 |
| 3 | Pass | 0.00 | 6.2 | 101 | 98.7 |
| 6 | Pass | 0.01 | 6.3 | 100 | 98.3 |
| 9 | Pass | 0.01 | 6.3 | 101 | 98.3 |
| 12 | Pass | 0.01 | 6.3 | 104 | 98.4 |
| 18 | Pass | 0.01 | 6.3 | 96 | 98.1 |
| 24 | Pass | 0.01 | 6.3 | 105 | 98.1 |

Example 2. Stability of 50 mg/ml VEGF Trap Liquid Formulation Stored at 5° C. in 3 ml Glass Vials A liquid formulation containing 50 mg/ml VEGF Trap (SEQ ID NO:4), 10 mM phosphate, 50 mM NaCl, 3% polyethylene glycol 3350, 5% sucrose, and pH 6.25, was stored at 5° C. in 3 nil glass vials and samples tested at 3, 6, 9, 12, 18 and 24 months. Stability results are shown in Table 2. Turbidity, percent recovered protein and purity was determined as described above.

TABLE 2

Stability of 50 mg/ml VEGF Trap Protein (VGFT-SS065)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 98.9 |
| 3 | Pass | 0.00 | 6.1 | 104 | 98.5 |
| 6 | Pass | 0.01 | 6.3 | 99 | 98.3 |
| 9 | Pass | 0.00 | 6.3 | 102 | 97.6 |
| 12 | Pass | 0.01 | 6.3 | 103 | 98.0 |
| 18 | Pass | 0.00 | 6.3 | 113 | 97.7 |
| 24 | Pass | 0.00 | 6.2 | 106 | 97.6 |

Example 3. Stability of 40 mg/ml VEGF Trap Liquid Formulation Stored at 5° C. in 3 ml Glass Vials A liquid formulation containing 40 mg/ml VEGF Trap (SEQ ID NO:4), 10 mM phosphate, 40 mM NaCl, 0.03% polysorbate 20, 5% sucrose, and pH 6.3, was stored at 5° C. in 3 ml glass vials and samples tested at 0.5, 1, 2, 3, and 4 months. Stability results are shown in Table 3. Turbidity, percent recovered protein and purity was determined as described above.

TABLE 3

Stability of 40 mg/ml VEGF Trap Protein (VGFT-SS207)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.5 |
| 0.5 | Pass | 0.00 | 6.3 | 99 | 99.4 |
| 1 | Pass | 0.00 | 6.2 | 98 | 99.5 |
| 2 | Pass | 0.00 | 6.2 | 95 | 99.2 |
| 3 | Pass | 0.01 | 6.4 | | |
| 4 | Pass | 0.01 | 6.3 | | |

Example 4. Stability of 40 mg/ml VEGF Trap Liquid Formulation Stored at 5° C. in Pre-Filled Glass Syringe A liquid formulation containing 40 mg/ml VEGF trap (SEQ ID NO:4), 10 mM phosphate, 40 mM NaCl, 0.03% polysorbate 20, 5% sucrose, and pH 6.3, was stored at 5° C. in 1 ml prefilled luer glass syringe with 4023/50 FluroTec coated plunger and samples tested at 0.5, 1, 2, 3, and 4 months. Stability results are shown in Table 4. Turbidity, percent recovered protein and purity was determined as described above.

TABLE 4

Stability of 40 mg/ml VEGF Trap Protein (VGFT-SS207)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.4 |
| 0.5 | Pass | 0.00 | 6.3 | 100 | 99.3 |
| 1 | Pass | 0.00 | 6.3 | 100 | 99.4 |
| 2 | Pass | 0.00 | 6.3 | 97 | 99.1 |
| 3 | Pass | 0.01 | 6.4 | | |
| 4 | Pass | 0.01 | 6.3 | | |

Example 5. Stability of 40 mg/ml VEGF Trap Liquid Formulation Stored at 5° C. in 3 ml Glass Vials A liquid formulation containing 40 mg/ml VEGF trap (SEQ ID NO:4), 10 mM phosphate, 135 mM NaCl, 0.03% polysorbate 20, and pH 6.3, was stored at 5° C. in 3 ml glass vials and samples tested at 0.5, 1, 2, 3, and 4 months. Stability results are shown in Table 5. Turbidity, percent recovered protein and purity was determined as described above.

TABLE 5

Stability of 40 mg/ml VEGF Trap Protein (VGFT-SS203)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.3 |
| 0.5 | Pass | 0.00 | 6.2 | 87 | 99.2 |
| 1 | Pass | 0.00 | 6.2 | 88 | 99.1 |
| 2 | Pass | 0.00 | 6.3 | 103 | 99.2 |
| 3 | Pass | 0.00 | 6.3 | 88 | 99.0 |
| 4 | Pass | 0.00 | 6.2 | 85 | 98.9 |
| 5 | Pass | 0.00 | 6.3 | 84 | 99.0 |

Example 6. Stability of 40 mg/ml VEGF Trap Liquid Formulation Stored at 5° C. in 1 ml Pre-Filled Glass Syringe A liquid formulation containing 40 mg/ml VEGF trap (SEQ ID NO:4), 10 mM phosphate, 135 mM NaCl, 0.03% polysorbate 20, and pH 6.3, was stored at 5° C. in 1 ml prefilled glass luer syringe with 4023/50 FluroTec coated plunger and samples tested at 0.5, 1, 2, 3, 4, and 5 months. Stability results are shown in Table 6. Turbidity, percent recovered protein and purity was determined as described above.

TABLE 6

Stability of 40 mg/ml VEGF Trap Protein (VGFT-SS203)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.2 |
| 0.5 | Pass | 0.01 | 6.3 | 101 | 99.2 |
| 1 | Pass | 0.00 | 6.3 | 101 | 99.2 |
| 2 | Pass | 0.00 | 6.3 | — | — |
| 3 | Pass | 0.01 | 6.3 | 102 | 99.1 |
| 4 | Pass | 0.01 | 6.3 | 103 | 98.8 |
| 5 | Pass | 0.00 | 6.3 | 99 | 98.9 |

Example 7. Stability of Lyophilized 20 mg/ml VEGF Trap Formulation Stored at 5° C. in 3 ml Glass Vials and Reconstituted to 40 mg/ml 0.8 ml of a liquid formulation containing 20 mg/ml VEGF trap (SEQ ID NO:4), 5 mM phosphate, 20 mM NaCl, 0.015% polysorbate 20, 2.5% sucrose, and pH 6.3, were lyophilized in 3 ml glass vials. Samples were stored at 5° C. and tested at 1, and 2 months. VEGF trap was reconstituted to a final concentration of 40 mg/ml VEGF Trap (final volume of 0.4 ml). Stability results are shown in Table 7 (t=time in months; *=visual appearance; **=reconstitution time). Turbidity, percent recovered protein and purity was determined as described above.

TABLE 7

Stability of Lyophilized 20 mg/ml VEGF Trap Protein (VGFT-SS216)

| t | Vis. App.* | Recon. Time** (min) | Vis. App.* Reconst'd Liquid | Turbidity | pH | % VEGF Trap Recovered | % VEGF Trap Native Config. |
|---|---|---|---|---|---|---|---|
| 0 | Pass | 0.6 | Pass | 0.00 | 6.3 | 100 | 99.5 |
| 1 | Pass | 0.6 | Pass | 0.01 | 6.3 | 106 | 99.4 |
| 2 | Pass | 0.4 | Pass | 0.01 | 6.2 | 103 | 99.3 |

Example 8. Stability of Lyophilized 20 mg/ml VEGF Trap Formulation Stored at 5° C. in 3 ml Glass Vials 0.8 ml of a liquid formulation containing 20 mg/ml VEGF trap (SEQ ID NO:4), 5 mM phosphate, 67.5 mM NaCl, 0.015% polysorbate 20, and pH 6.3, were lyophilized in 3 ml glass vials. Samples were stored at 5° C. and tested at 1, 2, and 3 months. VEGF trap was reconstituted to a final concentration of 40 mg/ml VEGF trap (final volume of 0.4 ml). Stability results are shown in Table 8 (t=time in months; *=visual appearance; **=reconstitution time).

TABLE 8

Stability of Lyophilized 20 mg/ml VEGF Trap Protein (VGFT-SS216)

| t | Vis. App.* | Recon. Time** (min) | Vis. App. Reconst'd Liquid | Turbidity | pH | % VEGF Trap Recovered | % VEGF Trap Native Config. |
|---|---|---|---|---|---|---|---|
| 0 | Pass | 0.7 | Pass | 0.00 | 6.3 | 100 | 99.0 |
| 1 | Pass | 0.7 | Pass | 0.01 | 6.2 | 105 | 98.9 |
| 2 | Pass | 0.4 | Pass | 0.01 | 6.2 | 103 | 98.9 |

We claim:

1. A vial containing a liquid formulation comprising:
   a glycosylated vascular endothelial growth factor (VEGF) antagonist fusion protein, comprising amino acids 27-457 of SEQ ID NO: 4 and glycosylated at asparagine residues corresponding to asparagine residues 62, 94, 149, 222 and 308 of SEQ ID NO: 4,
   polysorbate 20,
   sucrose, and
   a phosphate buffer at a pH of between 5.8 and 7.0 formulated as a mixture of mono and dibasic sodium phosphate in the absence of acid/base titration;
   wherein said VEGF antagonist fusion protein is substantially resistant to degradation and aggregation; and
   wherein said liquid formulation has a turbidity of 0.01 or lower at $OD_{405}$.

2. The vial of claim 1, wherein the concentration of said VEGF antagonist fusion protein is 40 mg/ml.

3. The vial of claim 2, wherein said phosphate buffer comprises a pH about 6.2-6.3.

4. The vial of claim 3, wherein said liquid formulation comprises about 0.03% to about 0.1% polysorbate 20.

5. The vial of claim 4, wherein said liquid formulation comprises 1.0-7.5% of sucrose.

6. The vial of claim 5, wherein said liquid formulation comprises 5-25 mM phosphate buffer.

7. The vial of claim 2, wherein said liquid formulation comprises 0.01% to 3% polysorbate 20.

8. The vial of claim 2, wherein said liquid formulation comprises 1.0-10% of sucrose.

9. The vial of claim 2, wherein said liquid formulation has a turbidity of 0.01 or lower at $OD_{405}$ after 2 month storage at 5° C.

10. The vial of claim 9, wherein said liquid formulation is an ophthalmic formulation suitable for intravitreal administration.

11. A vial containing a liquid formulation comprising:
   a glycosylated vascular endothelial growth factor (VEGF) antagonist fusion protein expressed in CHO cells and encoded by the nucleotide sequence of SEQ ID NO: 3,
   polysorbate 20,
   sucrose, and
   a phosphate buffer at a pH of between 5.8 and 7.0 formulated as a mixture of mono and dibasic sodium phosphate in the absence of acid/base titration;
   wherein said VEGF antagonist fusion protein is substantially resistant to degradation and aggregation; and
   wherein said liquid formulation has a turbidity of 0.01 or lower at $OD_{405}$.

12. The vial of claim 11, wherein the concentration of said VEGF antagonist fusion protein is 40 mg/ml.

13. The vial of claim 12, wherein said phosphate buffer comprises a pH about 6.2-6.3.

14. The vial of claim 13, wherein said liquid formulation comprises about 0.03% to about 0.1% polysorbate 20.

15. The vial of claim 14, wherein said liquid formulation comprises 1.0-7.5% of sucrose.

16. The vial of claim 15, wherein said liquid formulation comprises 5-25 mM phosphate buffer.

17. The vial of claim 12, wherein said liquid formulation comprises 0.01% to 3% polysorbate 20.

18. The vial of claim 12, wherein said liquid formulation comprises 1.0-10% of sucrose.

19. The vial of claim 12, wherein said liquid formulation has a turbidity of 0.01 or lower at $OD_{405}$ after 2 month storage at 5° C.

20. The vial of claim 19, wherein said liquid formulation is an ophthalmic formulation suitable for intravitreal administration.

21. A vial comprising
   an ophthalmic formulation suitable for intravitreal administration comprising
      40 mg/ml of a vascular endothelial growth factor (VEGF) antagonist fusion protein comprising amino acids 27-457 of SEQ ID NO: 4 and glycosylated at asparagine residues corresponding to asparagine residues 62, 94, 149, 222 and 308 of SEQ ID NO: 4,
      a buffer formulated in the absence of acid/base titration and comprising a pH of between 5.8 and 7.0,
      a stabilizing agent; and
   an inert gas;
   wherein 90% or more of the weight of said VEGF antagonist fusion protein is not present as an aggregate; and
   wherein the VEGF antagonist fusion protein is at least 95% free of protein contaminants.

22. The vial of claim 21, wherein the inert gas comprises nitrogen or argon.

23. The vial of claim 22, wherein said formulation does not contain phosphate.

24. The vial of claim 22, wherein said stabilizing agent comprises a sugar.

25. The vial of claim 24, wherein said sugar is selected from the group consisting of sucrose, sorbitol, glycerol, trehalose, and mannitol.

26. The vial of claim 24, wherein said stabilizing agent comprises 1.0-10% of sucrose.

27. The vial of claim 22, wherein said buffer comprises a phosphate buffer.

28. The vial of claim 22, wherein said buffer comprises 5-25 mM buffer.

29. The vial of claim 22, wherein the VEGF antagonist fusion protein is at least 99% free of protein contaminants.

30. The vial of claim 21, wherein said buffer comprises a pH about 6.2-6.3.

31. A vial comprising
an ophthalmic formulation suitable for intravitreal administration comprising
40 mg/ml of a glycosylated vascular endothelial growth factor (VEGF) antagonist fusion protein expressed in CHO cells and encoded by the nucleotide sequence of SEQ ID NO: 3,
a buffer formulated in the absence of acid/base titration and comprising a pH of between 5.8 and 7.0;
a stabilizing agent; and
an inert gas;
wherein 90% or more of the weight of said VEGF antagonist fusion protein is not present as an aggregate; and
wherein the VEGF antagonist fusion protein is at least 95% free of protein contaminants.

32. The vial of claim 31, wherein said buffer comprises a pH about 6.2-6.3.

33. The vial of claim 31, wherein the inert gas comprises nitrogen or argon.

34. The vial of claim 33, wherein said ophthalmic formulation does not contain phosphate.

35. The vial of claim 33, wherein said stabilizing agent comprises a sugar.

36. The vial of claim 35, wherein said sugar is selected from the group consisting of sucrose, sorbitol, glycerol, trehalose, and mannitol.

37. The vial of claim 35, wherein said stabilizing agent comprises 1.0-10% of sucrose.

38. The vial of claim 33, wherein said buffer comprises a phosphate buffer.

39. The vial of claim 33, wherein said buffer comprises 5-25 mM buffer.

40. The vial of claim 33, wherein the VEGF antagonist fusion protein is at least 99% free of protein contaminants.

41. A vial comprising a liquid ophthalmic formulation comprising:
a glycosylated vascular endothelial growth factor (VEGF) antagonist fusion protein comprising amino acids 27-457 of SEQ ID NO:4,
water,
a salt selected from the group consisting of sodium chloride, sodium phosphate, and combination thereof,
an organic co-solvent, and
a stabilizing agent,
wherein the formulation has a pH of between 5.8 and 7.0;
wherein the liquid ophthalmic formulation is suitable for intravitreal administration;
wherein 90% or more of the weight of said VEGF antagonist fusion protein is not present as an aggregate; and
wherein the VEGF antagonist fusion protein is at least 95% free of protein contaminants.

42. The vial of claim 41 wherein said salt is sodium chloride.

43. The vial of claim 41, wherein said salt is sodium phosphate.

44. The vial of claim 43, wherein said stabilizing agent comprises 1.0-10% of sucrose.

45. The vial of claim 44, wherein said organic co-solvent comprises polysorbate 20.

46. The vial of claim 41, wherein the concentration of said VEGF antagonist fusion protein is 40 mg/ml and said buffer comprises a pH about 6.2-6.3.

47. The vial of claim 46, wherein the VEGF antagonist fusion protein is at least 99% free of protein contaminants.

48. The vial of claim 41, wherein said stabilizing agent comprises a sugar.

49. The vial of claim 48, wherein said sugar is selected from the group consisting of sucrose, sorbitol, glycerol, trehalose, and mannitol.

50. The vial of claim 49, wherein said organic co-solvent comprises polysorbate.

51. A vial comprising a liquid aqueous ophthalmic formulation comprising:
a glycosylated vascular endothelial growth factor (VEGF) antagonist fusion protein expressed in CHO cells and encoded by the nucleotide sequence of SEQ ID NO: 3,
water,
a salt selected from the group consisting of sodium chloride, sodium phosphate, and combination thereof,
an organic co-solvent, and
a stabilizing agent,
wherein the formulation has a pH of between 5.8 and 7.0;
wherein the liquid ophthalmic formulation is suitable for intravitreal administration;
wherein 90% or more of the weight of said VEGF antagonist fusion protein is not present as an aggregate; and
wherein the VEGF antagonist fusion protein is at least 95% free of protein contaminants.

52. The vial of claim 51, wherein said salt is sodium chloride.

53. The vial of claim 51, wherein said salt is sodium phosphate.

54. The vial of claim 53, wherein said stabilizing agent comprises 1.0-10% of sucrose.

55. The vial of claim 54, wherein said organic co-solvent comprises polysorbate 20.

56. The vial of claim 51, wherein the concentration of said VEGF antagonist fusion protein is 40 mg/ml and said buffer comprises a pH about 6.2-6.3.

57. The vial of claim 56, wherein the VEGF antagonist fusion protein is at least 99% free of protein contaminants.

58. The vial of claim 51, wherein said stabilizing agent comprises a sugar.

59. The vial of claim 58, wherein said sugar is selected from the group consisting of sucrose, sorbitol, glycerol, trehalose, and mannitol.

60. The vial of claim 59, wherein said organic co-solvent comprises polysorbate.

* * * * *

UNITED STATES PATENT AND TRADEMARK OFFICE
CERTIFICATE OF CORRECTION

PATENT NO. : 11,732,024 B2
APPLICATION NO. : 17/348438
DATED : August 22, 2023
INVENTOR(S) : Eric Furfine et al.

Page 1 of 1

It is certified that error appears in the above-identified patent and that said Letters Patent is hereby corrected as shown below:

In the Claims

In Claim 3, Line 2: "pH about" should read -- pH of about --
In Claim 13, Line 2: "pH about" should read -- pH of about --
In Claim 30, Line 2: "pH about" should read -- pH of about --
In Claim 32, Line 2: "pH about" should read -- pH of about --
In Claim 41, Line 8: "combination thereof," should read -- combinations thereof, --
In Claim 46, Line 2: "pH about" should read -- pH of about --
In Claim 51, Line 8: "combination thereof," should read -- combinations thereof, --
In Claim 56, Line 2: "pH about" should read -- pH of about --

Signed and Sealed this
Twenty-third Day of April, 2024

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 1453
<212> TYPE: DNA
<213> ORGANISM: Artificial sequence
<220> FEATURE:
<223> OTHER INFORMATION: synthetic

<400> SEQUENCE: 1
aagcttgggc tgcaggtcga tcgactctag aggatcgatc cccgggcgag ctcgaattcg      60
caaccaccat ggtcagctac tgggacaccg ggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg gttacgtcac     240
ctaacatcac tgttactttta aaaagtttc cacttgacac tttgatccct gatggaaaac     300
gcataatctg ggacagtaga aagggcttca tcatatcaaa tgcaacgtac aagaaatag     360 ggcttctgac ctgtgaagca acagtcaatg gcatttgta taagacaaac tatctcacac     420
atcgacaaac caatacaatc atagatgtgg ttctgagtcc gtctcatgga attgaactat     480
ctgttggaga aaagcttgtc ttaaattgta gcaagaac tgaactaaat gtggggattg     540
acttcaactg ggaataccct tcttcgaagc atcagcataa gaaacttgta aaccgagacc     600
taaaaaccca gtctggggagt gagatgaaga aatttttgag caccttaact atagatggtg     660
taacccggag tgaccaagga ttgtacacct gtgcagcatc cagtgggctg atgaccaaga     720
agaacagcac atttgtcagg gtccatgaaa agggcccggg cgacaaaact cacacatgcc     780
caccgtgccc agcacctgaa ctcctgggg gaccgtcagt cttcctcttc cccccaaaac     840
ccaaggacac cctcatgatc tcccggaccc ctgaggtcac atgcgtggtg gtggacgtga     900
gccacgaaga ccctgaggtc aagttcaact ggtacgtgga cggcgtggag gtgcataatg     960
ccaagacaaa gccgcgggag gagcagtaca acagcacgta ccgtgtggtc agcgtcctca    1020
ccgtcctgca ccaggactgg ctgaatggca aggagtacaa gtgcaaggtc tccaacaaag    1080
ccctcccagc ccccatcgag aaaaccatct ccaaagccaa agggcagccc cgagaaccac    1140
aggtgtacac cctgccccca tcccgggatg agctgaccaa gaaccaggtc agcctgacct    1200
```

-continued

```
gcctggtcaa aggcttctat cccagcgaca tcgccgtgga gtgggagagc aatgggcagc      1260
cggagaacaa ctacaagacc acgcctcccg tgctggactc cgacggctcc ttcttcctct      1320
atagcaagct caccgtggac aagagcaggt ggcagcaggg gaacgtcttc tcatgctccg      1380
tgatgcatga ggctctgcac aaccactaca cgcagaagag cctctccctg tctccgggta      1440
aatgagcggc cgc                                                          1453
```

<210> SEQ ID NO 2
<211> LENGTH: 458
<212> TYPE: PRT
<213> ORGANISM: Artificial Sequence
<220> FEATURE:
<223> OTHER INFORMATION: synthetic

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
    50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
    130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
```

```
                305                 310                 315                 320
His Gln Asp Trp Leu Asn Gly Lys Glu Tyr Lys Cys Lys Val Ser Asn
                    325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Gly Lys
        450                 455

<210> SEQ ID NO 3
<211> LENGTH: 1377
<212> TYPE: DNA
<213> ORGANISM: Artificial Sequence
<220> FEATURE:
<223> OTHER INFORMATION: synthetic

<400> SEQUENCE: 3
atggtcagct actgggacac cggggtcctg ctgtgcgcgc tgctcagctg tctgcttctc      60
acaggatcta gttccggaag tgataccggt agaccttttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtgggggatt    480 gacttcaact gggaataccc ttcttcgaag catcagcata gaaacttgt aaaccgagac      540 ctaaaaaccc agtctgggag tgagatgaag aaatttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc ccgagaacca caggtgtac    1080 accctgcccc catcccggga tgagctgacc aagaaccagg tcagcctgac ctgcctggtc    1140
aaaggcttct atcccagcga catcgccgtg gagtgggaga gcaatgggca gccggagaac    1200
```

```
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga       1377
```

<210> SEQ ID NO 4
<211> LENGTH: 458
<212> TYPE: PRT
<213> ORGANISM: Artificial sequence
<220> FEATURE:
<223> OTHER INFORMATION: synthetic

<400> SEQUENCE: 4

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335
```

-continued

```
Lys Ala Leu Pro Ala Pro Ile Glu Lys Thr Ile Ser Lys Ala Lys Gly
            340             345                 350

Gln Pro Arg Glu Pro Gln Val Tyr Thr Leu Pro Pro Ser Arg Asp Glu
        355             360                 365

Leu Thr Lys Asn Gln Val Ser Leu Thr Cys Leu Val Lys Gly Phe Tyr
        370             375             380

Pro Ser Asp Ile Ala Val Glu Trp Glu Ser Asn Gly Gln Pro Glu Asn
385             390             395                 400

Asn Tyr Lys Thr Thr Pro Pro Val Leu Asp Ser Asp Gly Ser Phe Phe
            405             410              415

Leu Tyr Ser Lys Leu Thr Val Asp Lys Ser Arg Trp Gln Gln Gly Asn
        420             425             430

Val Phe Ser Cys Ser Val Met His Glu Ala Leu His Asn His Tyr Thr
        435             440             445

Gln Lys Ser Leu Ser Leu Ser Pro Gly Lys
    450             455
```